US00PP36589P2

(12) United States Plant Patent
Kapias

(10) Patent No.: US PP36,589 P2
(45) Date of Patent: Apr. 8, 2025

(54) BARBERRY PLANT NAMED 'JBN 17-001'

(50) Latin Name: *Berberis thunbergii*
Varietal Denomination: JBN 17-001

(71) Applicant: Capstone Plants, Inc., Grand Saline, TX (US)

(72) Inventor: Dariusz Kapias, Radostowice (PL)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 18/655,401

(22) Filed: May 6, 2024

(51) Int. Cl.
*A01H 5/00* (2018.01)
*A01H 6/00* (2018.01)

(52) U.S. Cl.
USPC ..... Plt./241
CPC ..... *A01H 6/00* (2018.05)

(58) Field of Classification Search
USPC ..... Plt./241
See application file for complete search history.

(56) References Cited

PUBLICATIONS https://buy-plants-at-j-berry-nursery.myshopify.com/products/purple-plume-barberry-1-gallon (Retrieved on the Internet on Aug. 19, 2024). (three pages total).*

International Code of Nomenclature for Cultivated Plants (ICNCP); Ninth Edition, Jun. 2016 (7 pages total).*

* cited by examiner

*Primary Examiner* — Susan McCormick Ewoldt
(74) *Attorney, Agent, or Firm* — The Webb Law Firm

(57) ABSTRACT

A new and distinct Barberry plant having reddish to dark purple foliage, high branching, and an upright growth habit.

3 Drawing Sheets

Botanical classification: *Berberis thunbergii.*
Varietal denomination: 'JBN 17-001'.

BACKGROUND OF THE INVENTION

The present invention comprises a new and distinct variety of Barberry plant having the varietal name 'JBN 17-001'. The new variety was discovered and selected in the Summer of 2012 in Radostowice, Poland as the result of a planned breeding program with the purposes of developing *Berberis thunbergii* plants that exhibit dark foliage with an upright growth habit that would be suitable to use as small hedges. 'JBN 17-001' is the result of open pollination between an unnamed and unpatented *Berberis thunbergii atropurpurea* variety from the breeder's own collection (female parent) and a group of unpatented *Berberis thunbergii* plants from the breeder's own collection. As such, the exact male parent from this collection is unknown.

The new variety was first asexually reproduced via cuttings in Grand Saline, Texas in April of 2018. The new variety is similar to its female parent in having red/purple leaves, but with a darker tone. Further, the new variety has the same hardiness zone as its female parent, but has stronger growth and a more upright growth habit. Unlike its female parent, the new variety has not exhibited the production of berries. Furthermore, the new variety differs from known Barberry varieties in its tighter and more upright growth form, with looser branching. In addition, the new variety differs from known Barberry varieties in its darker tone of its leaves and the lack of fruit.

The following traits distinguish 'JBN 17-001' as a new and distinct cultivar from other Barberry varieties known to the breeder:

1. Reddish to dark purple foliage;
2. Upright growth habit;
3. Improved disease resistance;
4. Looser branching; and
5. Lack of fruit.

1. DESCRIPTION OF THE DRAWINGS

The accompanying photographic images illustrate the new variety at approximately six months of age, with the colors being as nearly true as is possible with color illustrations of this type:

Figure 1:
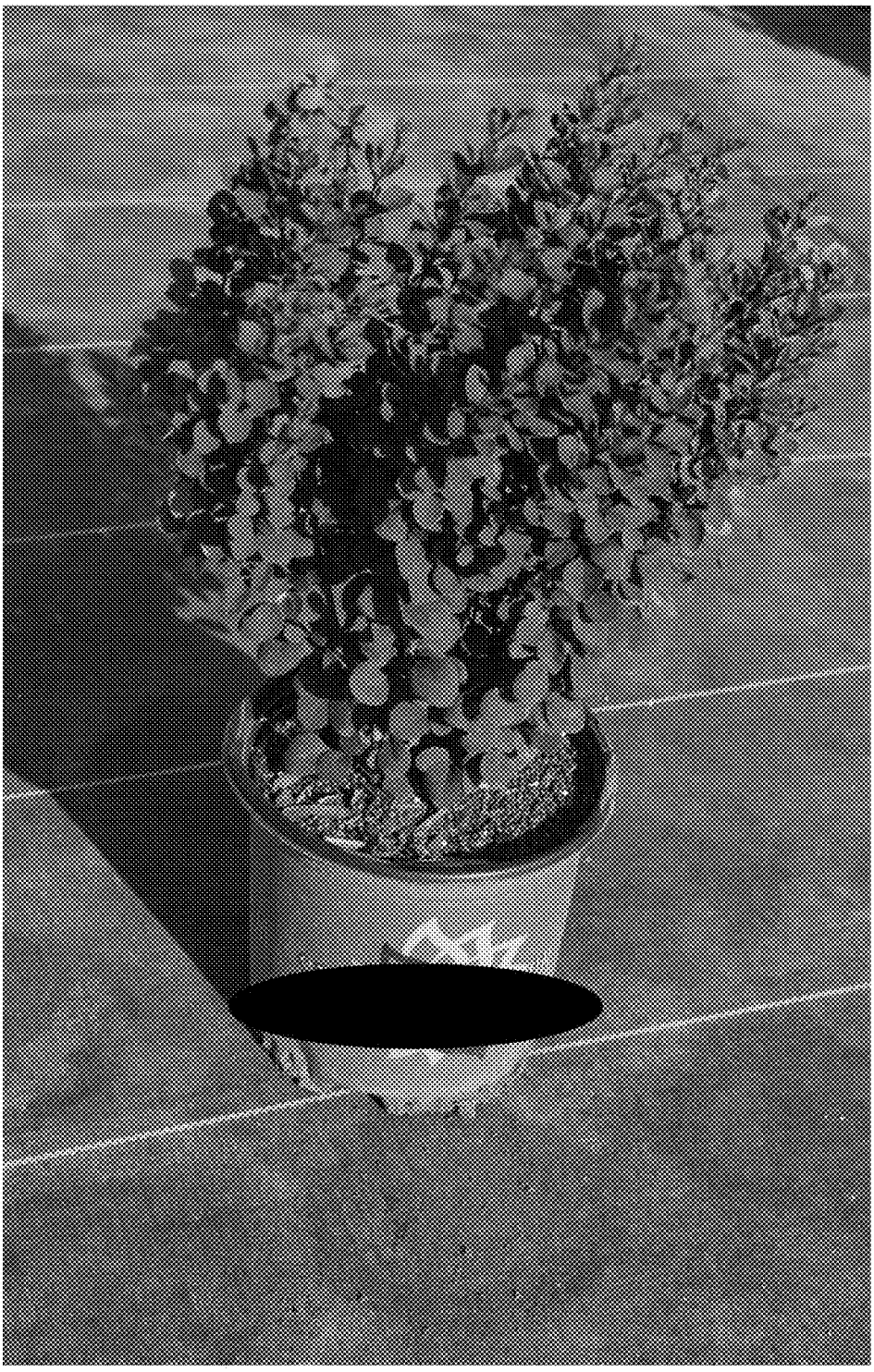
FIG. 1 illustrates an entire plant of the new variety.
Figure 2:
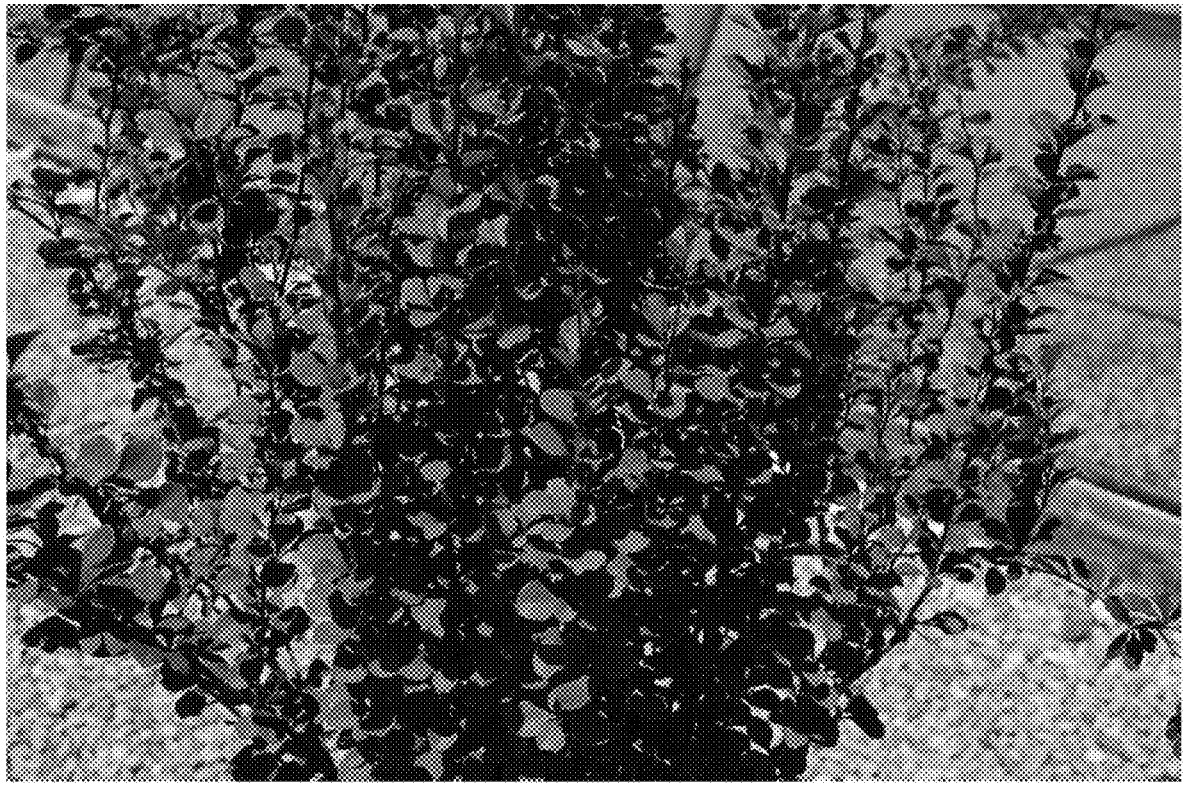
FIG. 2 illustrates a close-up view of the foliage of the new variety.
Figure 3:
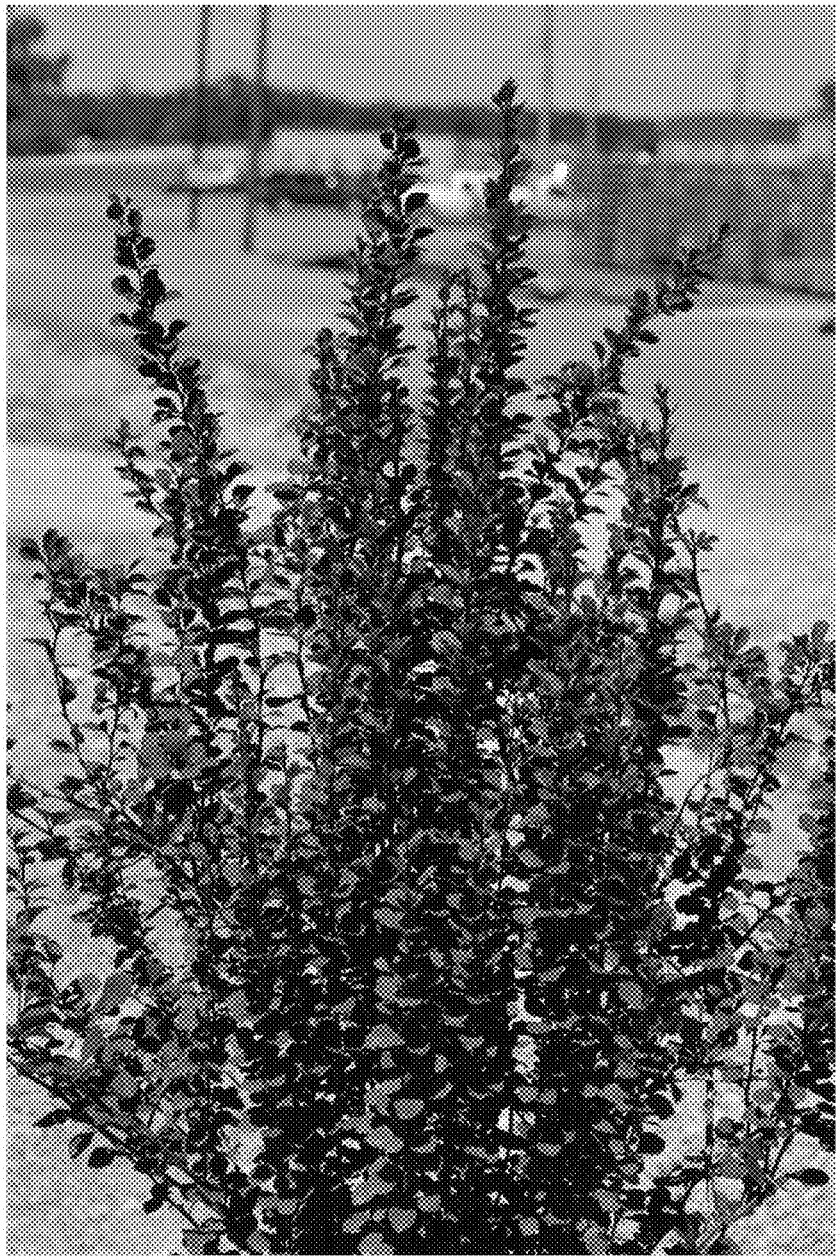

FIG. 3. illustrates the foliage of the new variety.

2. DESCRIPTION OF THE PLANT

The following detailed description sets forth the characteristics of the new variety as the result of asexual reproductions performed via cuttings carried out in Grand Saline, Texas. Plants of the new variety were grown outdoors in 20.0 cm (1 gallon/1.8 liter) pots under normal field production conditions, and the color readings and measurements were observed indoors under fluorescent lighting near natural lighting from a window on 6 month old plants in Grand Saline, Texas. Color references are primarily to The 1995 R.H.S. Colour Chart of The Royal Horticultural Society of London, Third Edition, except where terms of ordinary significance are used.

i) PLANT

Time to initiate roots: About 6-8 weeks at an average of 27-29° C.

Time to develop roots: About 18 weeks at an average of 27-29° C.

Heat/cold tolerance: 2023 USDA Hardiness Zone 8b.

Plant:

*Type*.—Deciduous, perennial foliage shrub.

*Habit*.—Upright.

*Height*.—Approximately 69.0 cm from top of soil to top of plant.

*Spread*.—Approximately 41.0 cm.

*Vigor*.—Moderate to high.

*Rooting*.—Fine and fibrous.

Branches:

*Number per plant*.—Approximately 49; well-branched.

*Length*.—From 30.0-66.0 cm.

*Width*.—From 2.0-4.0 mm.

*Texture*.—Coarse.

*Strength*.—High; very durable and strong.

*Internode length*.—1.5 cm.

*Color*.—Immature: RHS 187B. Mature: RHS 200A.

*Spines*.—Number per branch: From 42-83. Shape: Spinose. Length: From 5.0-7.0 mm. Width: Approximately 1.0 mm. Color: RHS 200C.

Foliage:

*Arrangement*.—Alternate.

*Size of leaf*.—Length: Approximately 2.5 cm. Width: Approximately 1.6 cm.

*Shape of leaf* (*generally*).—Obovate.

*Shape of apex*.—Acuminate.

*Shape of base*.—Cuneate.

*Texture*.—Upper surface: Very soft and smooth. Lower surface: Soft and smooth, but with a slight texture from venation.

*Margin type*.—Entire.

*Lobing*.—Not present.

*Color*.—Young leaves: Upper surface: RHS 187B, when foliage is covered by other leaves or other plants such that greater shade is provided, leaves exhibit 143C. Lower surface: RHS 183D. Mature leaves: Upper surface: RHS 187A. Lower surface: RHS 197A.

*Veins*.—Venation type: Pinnate. Color: Upper surface: RHS 187B. Lower surface: RHS 197A, with 183A towards the petiole.

*Petiole*.—Length: Approximately 4.0 mm. Diameter: Approximately 1.0 mm. Texture: Smooth. Color: RHS 187B.

Seeds: None observed.

I claim:

1. A new and distinct variety of *Berberis thunbergii* plant named 'JBN 17-001', substantially as illustrated and described herein.

* * * * *